United States Patent [19]

Miyake et al.

[11] 4,246,351

[45] Jan. 20, 1981

[54] PROTEIN ADSORBENT

[75] Inventors: Tetsuya Miyake, Tokyo; Kunihiko Takeda; Akihiko Ikeda, both of Yokohama; Masayuki Mizuno, Nobeoka, all of Japan

[73] Assignee: Asahi Kasei Kogyo Kabushiki Kaisha, Osaka, Japan

[21] Appl. No.: 88,927

[22] Filed: Oct. 29, 1979

Related U.S. Application Data

[60] Continuation of Ser. No. 942,716, Sep. 15, 1978, abandoned, which is a division of Ser. No. 841,271, Oct. 12, 1977, abandoned.

[30] Foreign Application Priority Data

Oct. 28, 1976 [JP] Japan .............................. 51/128868
May 10, 1977 [JP] Japan ................................ 52/52585

[51] Int. Cl.³ .............................................. C08J 9/00
[52] U.S. Cl. ...................................... 435/182; 260/8;
260/112 R; 260/112 B; 260/122; 435/180;
435/815; 521/53; 521/142; 521/146; 521/147;
521/149; 521/150
[58] Field of Search ..................... 435/180, 182, 815;
260/8, 112 R, 112 B, 122; 521/53

[56] References Cited

U.S. PATENT DOCUMENTS

| 3,418,262 | 12/1968 | Werotte et al. | 521/150 |
| 3,663,467 | 5/1972 | Albright | 521/150 |
| 3,767,600 | 10/1973 | Albright | 521/150 |
| 3,791,999 | 2/1974 | Fuchiwaki et al. | 521/150 |

Primary Examiner—Morton Foelak
Attorney, Agent, or Firm—Sprung, Felfe, Horn, Lynch & Kramer

[57] ABSTRACT

A novel protein adsorbent consisting essentially of a porous copolymer obtained by copolymerizing a monomer mixture comprising at least one cyano group-containing monomer and at least one cross-linkable monomer, said copolymer having an average pore diameter (d) of from 40 Å to 9,000 Å and a total pore volume of from $0.05\sqrt{X}$ ml to $1.5\sqrt{X}$ ml per gram of the copolymer in a dry state, in which X designates the weight proportion of said cross-linkable monomer expressed in terms of the percent by weight based on the total monomers. The present porous copolymer adsorbent has a remarkably high protein adsorbing capacity. The adorbent can advantageously be used for various purposes such as purification and separation of proteins, and removal of proteins. Copolymer-protein composites obtained by adsorption of proteins on the present porous copolymer also are industrially useful and have a wide variety of applications.

36 Claims, No Drawings

PROTEIN ADSORBENT

This is a continuation of application Ser. No. 942,716, filed Sept. 15, 1978 now abandoned which is in turn a division of application Ser. No. 841,271, filed Oct. 12, 1977, now abandoned.

This invention relates to a novel protein adsorbent. More particularly, the present invention is concerned with a protein adsorbent comprising a porous copolymer of a specific cyano-group containing monomer with a cross-linkable monomer, said porous copolymer being featured by the specific range of average pore diameter thereof and by the specific total pore volume thereof, thereby enabling its adsorbing capacity for proteins to be remarkably increased.

It is known that proteins are physically adsorbed on various substances, for example, inorganic substances such as activated carbon, silicic anhydride, celite, alumina, silica gel, hydroxylapatite, calcium phosphate and magnesium silicate, and natural polymeric substances such as starch, gluten and inulin. These substances have been practically used for clarification of protein-containing liquids, removal of proteins incorporated in minute amounts and purification or separation of proteins. However, the fact is that application ranges of respective adsorbents as mentioned above are remarkably limited for various reasons. For example, these substances often show specific characteristics to proteins, such as limited selectivity. In addition, solution conditions such as the pH value and/or the like at adsorption in which they are used are restricted. Furthermore, they occasionally cause a chemical reaction with some proteins or substances copresent therewith, and some of these adsorbents are insufficient in the mechanical strength.

Under such background, we made intensive researches and investigations with a view to developing a versatile protein adsorbent, and as a result, we found that a porous polyacrylonitrile type copolymer has a capacity of adsorbing various proteins in large quantities. Based on this finding, we have now completed the present invention.

More specifically, in accordance with the present invention, there is provided a protein adsorbent consisting essentially of a porous copolymer obtained by copolymerizing a monomer mixture comprising 2 to 98% by weight of at least one cyano group-containing monomer represented by the following general formula (A):

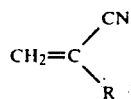

wherein R stands for a hydrogen atom, an alkyl group having 1 to 10 carbon atoms, a halogen atom, a cyano group, a methoxy group, an acetoxyl group, or an unsubstituted or substituted phenyl group represented by the formula

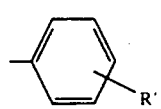

(wherein R' stands for a hydrogen atom, an alkyl group having 1 to 10 carbon atoms, a halogen atom, a cyano group, a methoxy group or an acetoxyl group), and 2 to 98% by weight of at least one cross-linkable monomer, said copolymer having an average pore diameter (d) of from 40 Å to 9,000 Å and a total pore volume of from $0.05\sqrt{X}$ ml to $1.5\sqrt{X}$ ml per gram of the copolymer in a dry state, in which X designates the weight proportion of said cross-linkable monomer expressed in terms of the percent by weight based on the total monomers.

As detailed hereinafter, the protein adsorbent of the present invention has a highly porous structure and a capacity of adsorbing a wide variety of proteins in large quantities. Further, the protein adsorbent of the present invention is chemically stable and it does not decompose proteins. Moreover, it has an excellent mechanical strength. Therefore, when the protein adsorbent of the present invention is employed, the adsorption process can be remarkably simplified and facilitated and the operation can be performed on an industrial scale with ease. Moreover, the protein adsorbent of the present invention can easily be prepared. These are advantages of the protein adsorbent of the present invention over the conventional protein adsorbents such as mentioned above.

As specific examples of the cyano group-containing monomer represented by the general formula (A), which constitutes one recurring unit of the copolymer of the protein adsorbent of the present invention, there can be mentioned acrylonitrile, methacrylonitrile, α-chloroacrylonitrile, vinylidene cyanide, α-bromoacrylonitrile, α-fluoroacrylonitrile, α-methoxyacrylonitrile, α-acetoxyacrylonitrile, α-ethylacrylonitrile, α-isopropylacrylonitrile, α-n-amylacrylonitrile, α-phenylacrylonitrile, α-(methoxyphenyl)acrylonitriles, α-tolylacrylonitriles, α-(chlorophenyl)acrylonitriles, α-(cyanophenyl)acrylonitriles, α-n-hexylacrylonitrile, α-neopentylacrylonitrile and the like. They may be employed alone or in mixture. The content of the cyano group-containing monomer in the copolymer is 2 to 98%, preferably 4 to 95% and especially preferably 6 to 90% by weight.

The preferred content of the cyano group-containing monomer depends greatly on properties of a protein to be adsorbed or a solution containing a protein to be adsorbed. However, in general, if the content of the cyano group-containing containing monomer is excessive, the degree of crosslinking is lowered and there are caused such disadvantages is instability of the porous structure, excessive swelling or contraction and reduction of the mechanical strength. On the other hand, if the content of the cyano group-containing monomer is too small, no sufficient adsorbing effect can be attained in the resulting adsorbent. Accordingly, the use of too large or too small an amount of the cyano group-containing monomer is not preferred.

The copolymer of the present invention may comprise other monomer or monomers copolymerizable with the cyano group-containing monomer. As such monomers, there can be mentioned, for example, hydrocarbon compounds such as styrene, methylstyrenes, ethylstyrenes, vinylnaphthalenes, butadiene, isoprene, piperylene and the like; styrene derivatives such as chlorostyrenes, bromostyrenes, N,N-dimethylaminostyrenes, nitrostyrenes, chloromethylaminostyrenes and the like; vinyl sulfide derivatives such as methyl vinyl sulfide, phenylvinyl sulfide and the like; acrylic acid; methacrylic acid; itaconic acid; acrylic acid esters such as methyl acrylate, chloromethyl acrylate and the like; methacrylic acid esters such as cylohexyl methacrylate, dimethylaminoethyl methacrylate, glycidyl methacrylate, tetrahydrofurfuryl methacrylate, hydroxyethyl methacrylate and the like; itaconic acid esters such as dimethyl itaconate, diethyl itaconate, di-n-butyl itaconate and the like; vinyl ketones such as methyl vinyl ketone, ethyl isopropenyl ketone and the like; vinylidene compounds such as vinylidene chloride, vinylidene bromide and the like; acrylamide derivatives such as acrylamide, N-butoxymethyl acrylamide, N,N-dimethylaminoethyl acrylamide and the like; vinyl esters of fatty acids such as vinyl acetate, vinyl caprate and the like; thio-fatty acid derivatives such as methyl thioacrylate, vinyl thioacetate and the like; and heterocyclic vinyl compounds such as N-vinylsuccinimide, N-vinylpyrrolidone, N-vinylphthalimide, N-vinylcarbazole, vinylfurans, vinylimidazoles, methylvinylimidazoles, vinylpyrazoles, vinyloxazolidones, vinylthiazoles, vinylpyridines, methylvinylpyridines, 2,4-dimethyl-6-vinyltriazine and the like. They may be employed alone or in mixture.

The term "cross-linkable monomer" as used herein is intended to mean a monomer having a plurality of $CH_2'C<$ groups. As specific examples of the cross-linkable monomer which constitutes the other recurring unit of the copolymer of the protein adsorbent of the present invention, there can be mentioned divinylbenzenes, divinyltoluenes, divinylxylenes, divinylnaphthalenes, divinylethylbenzenes, trivinylbenzenes, divinyldiphenyls, divinyldibenzyls, divinylphenyl ethers, divinyldiphenylamines, divinyl sulfone, divinyl ketone, divinylpyridines, divinylquinolines, diallyl phthalate, diallyl maleate, diallyl fumarate, diallyl carbonate, diallyl oxalate, diallyl adipate, diallyl tartrate, diallylamine, triallylamine, triallyl phosphate, triallyl tricarballylate, N,N'-ethylenediacrylamide, N,N'-methylenedimethacrylamide, ethylene glycol dimethacrylate, polyethyene glycol dimethacrylate, 1,3-butylene glycol dimethacrylate, dipropylene glycol dimethacrylate, polyethylene glycol diacrylate, polypropylene glycol diacrylate, trimethylolpropane trimethacrylate, pentaerythritol tetramethacrylate, 1,3-butylene glycol diacrylate, trimethylol propane triacrylate, pentaerythritol tetraacrylate, triallyl isocyanurate, 1,3,5-triacryloylhexahydro-1,3,5-triazine, diallylmelamine and the like. They may be employed alone or in mixture. Among these monomers, monomers having 2 to 4 vinyl groups are preferred. Cross-linkable monomers such as hydrocarbon type cross-linking agents, e.g., divinylbenzenes, and fatty acid ester type cross-linking agents, e.g., ethylene glycol dimethacrylate, are especially preferred. For example, fatty acid ester type cross-linkable agents are represented by the following general formula (B):

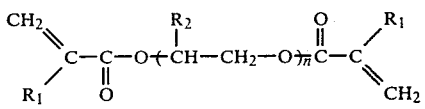

wherein $R_1$ and $R_2$ stand for a hydrogen atom or a methyl group, and n is an integer of from 1 to 30.

The content of the cross-linkable monomer is 2 to 98%, preferably 5 to 90% and especially preferably 8 to 80% by weight. When the content of the cross-linkable monomer is too low, swelling or contraction is unfavorably increased and the mechanical strength is decreased. On the other hand, if the content of the cross-linkable monomer is too high and the degree of cross-linking is excessively increased, the velocity of diffusion of a protein into pores of the copolymer is reduced.

The copolymer constituting the protein adsorbent of the present invention has a porous structure including an innumerable number of pores having an average pore diameter within the range of from 40 Å to 9,000 Å, preferably from 50 Å to 5,000 Å and especially preferably from 60 Å to 3,000 Å. If the average pore diameter is too small, intrusion or adsorption of a protein into pores of the copolymer becomes impossible or the diffusion velocity is largely reduced. Too large an average pore diameter results in such disadvantages as diminution of the surface area having a great influence on the adsorbing capacity and reduction of the mechanical strength.

Also the pore diameter distribution is a factor having a significant influence on the adsorbing capacity. It is preferred that the volume of pores having a diameter of 0.5 d to 2 d (in which d designates the average pore diameter) is not more than 60%, especially not more than 50%, of the total pore volume. Although there is specified no lower limit of this value, since the volume of pores having diameter approximating to the average pore diameter should naturally be large, the lower limit of the above value is inevitably 20% or more and in general, the lower limit is 30%. As will be apparent from the illustration given hereinafter, the porous copolymer of the present invention having such a broad pore diameter distribution range has a very high protein-adsorbing capacity.

Also the pore volume is a factor having significant influence on the protein-adsorbing capacity. More specifically, in the present invention, it is indispensable that the total pore volume is in the range of from $0.05\sqrt{X}$ ml to $1.5\sqrt{X}$ ml per gram of the dry copolymer, in which X stands for the weight proportion of the cross-linkable monomer expressed in terms of the percent by weight based on the total monomers, and it is preferred that the total pore volume is in the range of from $0.2\sqrt{X}$ ml to $1.3\sqrt{X}$ ml per gram of the dry copolymer. When the pore volume is too small, no sufficient adsorbing surface is provided. If the pore volume is too large, not only the mechanical strength of the copolymer is decreased but also the adsorbing capacity, namely the amount of a protein that can be adsorbed per unit volume of the copolymer, is rather reduced. In the case of the latter, the copolymer is liable to deformation, and therefore, when it is used in a column method, the pressure drop is often extraordinarily increased to such an extent that a solution of the protein cannot pass through the column.

Methods adopted in the present invention for the determination of pore characteristics will now be described.

The average pore diameter, pore diameter distribution and pore volume are measured using a mercury penetration porosimeter. More specifically, mercury is forced, under increasing pressure, into pores of a porous material to be measured and the pore volume is determined from the amount of mercury occluded in pores of the sample, and the pore diameter is calculated based on the principle that the diameter of a pore is in inverse proportion to the pressure necessary for forcing mercury into the pores. This measurement method is detailed in Chapter 10 of "Fine Particle Measurement" written by Clyde Orr, Jr. and J. M. Dallavalle and published by The Macmillan Company, New York in 1959, and in "Industrial and Engineering Chemistry"

vol. 17, No. 12, 1945, p. 782 to 786, written by H. L. Ritter and L. C. Drake. The measurement was conducted basically in accordance with ANSI/ASTM D2873-70 (Reapproved 1976), using Mercury Penetration Porosimeter, Model 905-1 (manufactured and sold by Micromeritics Instrument Corporation, U.S.A.). Penetration volume readings were obtained by forcing mercury into the pores at the pressures (psi) in the following list.

| | | | | |
|---|---|---|---|---|
| 14.7 | 100 | 450 | 2,000 | 10,000 |
| 20 | 125 | 650 | 3,000 | 15,000 |
| 35 | 175 | 850 | 4,000 | 20,000 |
| 45 | 250 | 1,150 | 5,000 | 30,000 |
| 85 | 350 | 1,500 | 7,000 | 40,000 |
| | | | | 50,000 |

According to this method, even pores having a pore diameter as small as 35-40 Å can be measured. In the present invention, the term "pore" is intended to mean an open pore communicated to the outside surface of the copolymer and having a pore diameter of at least 40 Å, and the pore volume is determined with respect to such open pores. The penetrometer readings versus the total absolute pressure was plotted on four phase semi-log graph paper and the points were connected using a French curve. The obtained curve represent a profile of the apparent interval pore size distribution. The "average pore diameter" is defined to be a value of r providing a maximum value of dV/d log r in the obtained curve, in which r represents the pore diameter and V denotes the cumulative pore volume measured by the mercury penetration porosimeter. In the present invention, the "total pore volume" is defined to be the volume of mercury forced in the pores of 1 g. of the sample dry copolymer during the period in which the mercury pressure is increased from 56 psi to 50,000 psi in the mercury penetration method.

The bulk density can be mentioned as another index of porosity. In the present invention, the bulk density was determined according to the following method:

A sample copolymer was filled in a column equipped with a glass filter, and water was sufficiently flowed through the column and the volume of the sample-packed portion of the column was measured. Then, the sample was sufficiently dried and its weight was measured. The bulk density was calculated by dividing the weight by the volume.

One of methods for preparing adsorbent copolymers of the present invention will now be described.

There has heretofore been developed and proposed a method for preparing highly porous cross-linked copolymers (see U.S. patent application Ser. No. 677,120, West German patent application No. P 2,618,481.6, British patent application No. 17,664/76 and French patent application No. 76-11919). This method can be effectively applied to the preparation of porous copolymers of the present invention. That is, the protein adsorbent of the present invention can be produced by copolymerizing a monomer mixture comprising 2 to 98% by weight of at least one cyano group-containing monomer represented by the following general formula (A):

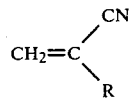 (A)

wherein R stands for a hydrogen atom, an alkyl group having 1 to 10 carbon atoms, a halogen atom, a cyano group, a methoxy group, an acetoxyl group, or an unsubstituted or substituted phenyl group represented by the formula

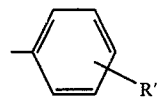

(wherein R' stands for a hydrogen atom, an alkyl group having 1 to 10 carbon atoms, a halogen atom, a cyano group, a methoxy group or an acetoxyl group), and 2 to 98% by weight of at least one cross-linkable monomer, in the presence of an organic medium which does not react with any of the monomers, and selected from the group consisting of (I) a mixed organic medium consisting essentially of at least one liquid selected from Group (i) liquids and at least one other liquid selected from Group (iii) liquids;

(II) a mixed organic medium consisting essentially of at least one liquid selected from Group (ii) liquids and at least one other liquid selected from Group (iii) liquids;

(III) an organic medium consisting of one liquid selected from Group (iii) liquids; and (IV) a mixed organic medium consisting of at least two liquids selected from Group (iii) liquids; wherein Group (i) liquids dissolve all of the homopolymers of the monomers chosen;

Group (ii) liquids do not dissolve any of the homopolymers chosen, and

Group (iii) liquids dissolve at least one homopolymer of the monomers chosen but do not dissolve at least another homopolymer of the monomers chosen.

In the present invention, the following method is employed for selecting an organic liquid.

To one organic liquid is added 5 percent by weight of one monomer and 0.1 percent by weight of 2,2-azobisisobutyronitrile and the resulting solution is polymerized in a sealed glass tube for 8 hours at the same temperature as is to be used for the polymerization reaction of this invention, and then the reaction mixture is observed. When the resulting polymer is precipitated, the organic liquid is denoted an "orgaic liquid which does not dissolve a homopolymer of the monomer", and when the resulting polymer is dissolved in the organic liquid, the organic liquid is denoted an "organic liquid which dissolves a homopolymer of the monomer". Also, with regard to one cross-linkable monomer having a plurality of $CH_2=C<$ groups employed as the monomer, when the reaction mixture of the resulting polymer and the organic liquid is opaque, the organic liquid is denoted an "organic liquid which does not dissolve a homopolymer of the monomer," and when the reaction mixture is transparent, the organic liquid is denoted an "organic liquid which dissolves a homopolymer of the monomer".

The solubilities of certain polymers in organic liquids are described in J. Brandrup and E. H. Immergut, *Poly-* mer *Handbook,* Chap. IV, pages 185–234 (1966) and Chap. IV, pages 241–265, Second Edition (1975) which is useful when selecting solvents and non-solvents.

It is generally said that the solubility of polymers in organic liquids is evaluated by the relative value of the respective solubility parameters. This method, however, can only be applied to polymers having a comparatively low polarity, and when such a method is applied to polymers comprising a polar monomer unit such as a cyano group-containing monomer unit, the selection of organic liquids according to solubility parameters often leads to errors.

The process for the preparation of a copolymer having a desired porous structure will now be explained.

Firstly, the desired pore diameter can be obtained in accordance with the following procedures. The polymerization is carried out using an organic medium containing at least one appropriate liquid selected from Group (iii) liquids. When the pore diameter of a polymer obtained is smaller than that desired, it can be increased by adding at least one liquid selected from Group (ii) liquids to the organic medium. When the pore diameter is greater than that desired, it can be decreased by adding at least one liquid selected from Group (i) liquids to the organic medium. When an organic medium containing at least two liquids selected from Group (iii) liquids is employed, the pore diameter can be controlled precisely. Generally, when there are employed a plurality of liquids, the pore diameter in the resulting copolymer can be continuously changed by appropriately changing the mixing ratio of the liquids.

Secondly, the desired pore volume can be obtained by controlling following conditions. The pore volume of the resulting copolymer depends on its pore diameter and on the amount of the organic medium employed. When the pore diameter is small, most of the organic medium is consumed for swelling of the polymer network and, as a result, the pore volume is decreased. On the other hand, as the proportion of the cross-linkable monomer to the total monomers is increased, it is required for securing the sufficient pore volume to increase the amount of the organic medium to be added. One of the reasons for this is that while swelling tendency of a low cross-linked copolymer in an aqueous solution leads to increase of its pore volume, a high cross-linked copolymer has less such tendency and therefore the increase of its pore volume due to swelling in an aqueous solution is smaller. Another reason is that the higher the degree of cross-linking, the denser the three-dimensional structure of the polymer chain of the resulting copolymer becomes and therefore, the harder it becomes to form micropores which provide adsorption sites for a protein to be adsorbed thereon. More specifically, if the percent by weight of the total liquids based on the total monomers is designated as D and the percent by weight of the cross-linkable monomer based on the total monomers is designated as X, it is preferred that the condition of $7\sqrt{X} < D < 500\sqrt{X}$ is satisfied, and it is more preferred that the condition of $20\sqrt{X} < D < 200\sqrt{X}$ especially $34\sqrt{X} < D < 150\sqrt{X}$ is satisfied.

Specific examples of combinations of liquids to be used for the preparation of copolymers of the present invention will now be mentioned.

In case of copolymerization of acrylonitrile with divinylbenzene and ethylstyrene, dimethylformamide, N-methylacetamide, nitromethane, dimethylsulfoxide, benzonitrile, α-butyrolactone, N,N-dimethylacetamide, acetophenone and the like can be used as Group (i) liquid; aromatic hydrocarbons such as toluene, xylene, ethylbenzene, tetralin and the like, cyclohexanone, anisole, chlorobenzene, dichlorobenzenes, methyl benzoates, ethyl benzoates, benzyl alcohol, methylene chloride, chloroform, dioxane and the like can be used as Group (iii) liquid; and aliphatic hydrocarbons such as heptane and decalin and the like, aliphatic alcohols such as n-butanol, cyclohexanol, isooctyl alcohol and the like, amyl acetate, dibutyl phthalate, dioctyl phthalate and the like can be used as Group (ii) liquid.

In case of copolymerization of acrylonitrile with ethylene glycol dimethacrylate; dimethylformamide, dimethylsulfoxide, α-butyrolactone, N,N-dimethylacetamide and the like can be used as Group (i) liquid; toluene, methyl ethyl ketone, dioxane, cyclohexanone, methylene chloride, chlorobenzene and the like can be used as Group (iii) liquid; and heptane, octane, n-butanol and isopropanol can be used as Group (ii) liquid.

In case of copolymerization of methacrylonitrile with divinylbenzene and ethylvinylbenzene; pyridine, nitromethane, benzonitrile, cyclohexanone, methyl ethyl ketone, α-butyrolactone and the like can be used as Group (i) liquid; toluene, ethylbenzene, tetralin, butyl acetate, ethyl propionate and the like can be used as Group (iii) liquid; and heptane, butanol, isooctanol, cyclohexanol, dioctyl phthalate and the like can be used as Group (ii) liquid.

In addition to the above-exemplified liquids, a wide variety of other liquids can be used, after dissolving characteristics of these liquids have been examined.

The polymerization for preparing copolymers of the present invention can be accomplished according to either the radical polymerization method or the ionic polymerization method, but in general, it is recommended to adopt a polymerization method comprising heating a solution or an aqueous suspension of a medium-monomer mixture containing a radical initiator dissolved therein. A radical initiator soluble in a mixture of the medium and monomers and capable of decomposition at a reaction temperature is employed for the radical polymerization. As preferred examples of the radical initiator, there can be mentioned acyl peroxides such as benzoyl peroxide, lauroyl peroxide and the like, azonitriles such as 2,2'-azobisisobutyronitrile,1,1'-azobis (cyclohexane carbonitrile) and the like, peroxides such as di-tert-butyl peroxide, dicumyl peroxide, methyl ethyl ketone peroxide and the like, and hydroperoxides such as cumene hydroperoxide and tert-butyl hydroperoxide and the like. The reaction is carried out at temperatures of 10° to 200° C., preferably 20° to 150° C. and especially preferably 30° to 100° C. When monomers including acrylonitrile are polymerized in the open system, since the boiling point of acrylonitrile is low, it is necessary to lower the polymerization temperature. Accordingly, in this case, it is preferred to use as a part or all of the polymerization initiator an initiator of the low temperature decomposition type, for example, 2,2'-azobis(2,4-dimethylvaleronitrile), 2,2'-azobis(4-methoxy-2,4-dimethylvaleronitrile), tert-butyl pervalerate, di-isobutyl peroxocarbonate or the like.

The most preferred polymerization method for synthesis of copolymers of the present invention is suspension polymerization using water as a suspension medium, by which a granular resin can easily be obtained. Acrylonitrile has a slight solubility in water, but when acrylonitrile is mixed with a water-insoluble liquid or monomer, the solubility in water is drastically reduced.

In case a water-soluble organic liquid or monomer is employed in practicing polymerization, the suspension polymerization method is not recommended. In this case, it is preferred to adopt a method in which a bulky product is first prepared by the solution polymerization and it is then pulverized to a suitable grain size.

As the suspending agent that can be used in the present invention, there can be mentioned, for example, natural polymeric substances such as starch, tragacanth gum, gelatin and the like; modified natural polymeric substances such as hydroxyethyl cellulose, methyl cellulose, carboxymethyl cellulose and the like; water-soluble synthetic polymeric substances such as polyacrylic acid, polyvinyl pyrrolidone, partially saponified polyvinyl acetate, polyvinyl alcohol and the like, and inorganic substances such as barium sulfate, talc, hydroxylapatite, bentonite, silicic anhydride, calcium carbonate and the like.

When a slightly water-soluble organic liquid or monomer such as acrylonitrile is employed, in order to control its slight solubility, it is preferred to add an inorganic salt such as sodium chloride, calcium chloride or the like to the aqueous phase.

The cyano group-containing, porous cross-linked copolymer of the present invention which is prepared according to the above-mentioned typical method was found to have very excellent properties as the protein adsorbent. These excellent properties will now be described one by one.

(1) The adsorbent of the present invention has a highly porous structure.

The performance of an adsorbent will be evaluated first of all by the adsorption velocity and adsorption capacity. Accordingly, not a few conventional adsorbents having a porous structure are available. One of characteristic features of the adsorbent of the present invention over such conventional adsorbents is that the porous structure can optionally be adjusted and modified. For example, in the copolymer of the present invention, the average pore diameter can optionally be set within the range of from 40 Å to 9,000 Å. On the other hand, it is preferred that the pore diameter distribution range is broad to some extent. The presence of large-diameter pores enhances remarkably the velocity of diffusion of a protein into the pores of the copolymer and when small-diameter pores are present in large quantities, the inner surface area of the copolymer is increased. It has been found that the copolymer of the present invention having a relatively broad pore diameter distribution range has a high adsorption velocity and a high adsorption capacity. When a certain protein is to be adsorbed, there will be present a porous structure optimum for adsorption of said protein. Guidelines for obtaining an optimum porous structure cannot be given simply, but what must be first taken into consideration for obtaining an optimum porous structure will be the molecular size of a protein to be adsorbed. In general, proteins have a molecular size in the range of about ten angstroms to several hundreds of angstroms. In order to allow the protein to diffuse into the pores of the copolymer and in order to adsorb the protein in the porous structure, it is required to form in the copolymer pores having a diameter larger than at least the molecular size of the protein.

It has been found that an optimum average pore diameter is present depending on the molecular size of a protein to be adsorbed. For example, the experimental results of Examples 8 to 12 given hereinafter suggest that proteins having a molecular weight lower than about 80,000 are adsorbed in largest quantities on a copolymer having an average pore diameter of 200 Å while proteins having a molecular weight higher than about 100,000 are adsorbed in large quantities on a copolymer having an average pore diameter of 1,200 Å. Namely, it is taught by the results that when the molecular size of a protein is large, the large pore diameter is necessary so that the protein may be sufficiently diffused. More specifically, an optimum porous structure can be obtained by providing in the copolymer appropriate pore characteristics depending on the molecular size and shape of a protein to be adsorbed, and occasionally, it is possible to selectively adsorb a specific protein alone among a plurality of proteins.

(2) The copolymer adsorbent of the present invention has a capacity of adsorbing various proteins in large quantities.

From results obtained in Examples given hereinafter, it is apparent that various proteins ranging from peptides having a molecular weight of about 1,000 to macromolecular proteins having a molecular weight of several hundreds of thousands can be adsorbed by the adsorbent of the present invention in such large quantities as some 100 mg per gram of the dry copolymer. In addition, the protein-adsorbing capacity of the copolymer of the present invention is not influenced at all by the isoelectric point, which is regarded as another important factor characterizing the protein. For example, in Examples 8 to 12, it is shown that the copolymer of the present invention has a very high adsorbing capacity to a variety of proteins having an isoelectric point in the wide range of from 4.7 to 10.4.

It has been found that the copolymer adsorbent of the present invention has a high adsorbing capacity to enzymes as well as ordinary simple proteins.

(3) The copolymer adsorbent of the present invention is characterized by a high mechanical strength.

Polymers derived from starch, cellulose, dextran and the like have heretofore been widely used as carriers for separation, purification and fixation of proteins. Typical instances of such polymers are cross-linked dextran marketed under the tradename "Sephadex" (Pharmacia Fine Chemicals AB, Sweden) and cross-linked agarose marketed under the tradename "Sepharose" (Pharmacia Fine Chemicals AB, Sweden). These carriers derived from natural substances, however, have a high degree of swelling and are inferior in the mechanical strength. Accordingly, they are readily deformed or crushed under pressure and permeation of protein-containing liquids is often inhibited by increase of pressure. Therefore, they can hardly be used on a large industrial scale. In contrast, the adsorbent of the present invention has a high mechanical strength inherent to a three-dimensional cross-linked polymer. Accordingly, the copolymer of the present invention can be advantageously used for chromatography in the state packed in a column.

(4) It is well-known in the art that in view of the adsorbing capacity, the mechanical strength and the easiness of passage of a liquid, it is most preferred that adsorbents have a spherical shape. According to the present invention, a protein adsorbent composed of a copolymer having a spherical shape can easily be prepared by suspension polymerization using water as a suspension medium.

(5) One of the preferred properties of an adsorbing resin is that the resin is inactive and can be used in a broad pH range. Since polyacrylonitrile, polydivinylbenzene and the like impart this property, the copolymer of the present invention satisfies this property unless a monomer having a high reactivity is incorporated in the starting monomer mixture. Versatile inorganic adsorbents such as activated alumina and silica gel sometimes decompose an adsorbate. In contrast, the protein adsorbent of the present invention is advantageous over these versatile inorganic adsorbents because the copolymer adsorbent of the present invention can be applied to a wide variety of substrates under wide-ranging operation conditions.

(6) Still further, the copolymer of the present invention can be used repeatedly and the adsorbing capacity can be maintained at a high level for a long time with less degradation. Accordingly, the protein adsorbent of the present invention has a very high practical utility.

As will be apparent from the foregoing illustration, the protein adsorbent of the present invention has various preferred characteristics. One of the reasons will be that the cross-linkable monomer is included in the structural units of the copolymer constituting the protein adsorbent of the present invention. A cyano group-containing porous composition can be obtained, for example, by adding a polymer solution including polyacrylonitrile to a nonsolvent to precipitate the polymer or by depositing polyacrylonitrile on the surface of a porous substance, for example, according to a method comprising contacting a solution of polyacrylonitrile with the porous substance and removing the solvent by evaporation. The copolymer of the present invention having a three-dimensional cross-linked structure is advantageous over such porous products in various points. For example, the porous structure in the copolymer of the present invention can easily be set and adjusted and the once formed porous structure is changed or deformed to a lesser extent by passage of liquids or application of external pressure. Accordingly, the copolymer of the present invention shows a high adsorbing capacity stably for a long time. Moreover, the protein adsorbent of the present invention has a high mechanical strength and the copolymer constituting the protein adsorbent of the present invention is not dissolved in liquids to be treated.

The term "dry copolymer" or "copolymer in a dry state" as used herein is intended to mean the copolymer of which the weight has become substantially constant upon the following drying process. After copolymerization, the obtained copolymer is sufficiently washed with a solvent having a boiling point not higher than 120° C., and then dried at 70° C. The weight of the copolymer is measured at prescribed intervals. When the difference between two measured weights of the copolymer at an interval of 24 hours is less than 1% of the later measured weight, the copolymer is regarded as the copolymer of which the weight has become substantially constant. Drying may be conducted under reduced pressure so as to shorten the drying time.

In the present invention, "protein" means a macromolecular nitrogen-containing compound having a molecular weight of not less than 500 which compound is essentially composed of a plurality of $\alpha$-amino acids bonded together through acid amide bond, namely peptide bond.

Examples of proteins to be adsorbed by the adsorbent of the present invention include avidin; albumins such as serum albumin, ovalbumin, conalbumin, lactalbumin, leucosin, ricin, legumelin and the like; erythrocruorin; phosphoproteins such as casein, vitellin, phosvitin and the like; globulins such as serum globulins, ovoglobulin, lactoglobulin, legumin, edestin, phaseolin, glycinin and the like; protamines such as salmine, clupeine and the like; myoproteins such as myosin, actin, tropomysin, myogen and the like; histone; prothrombin; hemerythrin; hemoglobin; hemocyanin; myoglobin; lipoproteins such as rhodopsin, lipovitellin, proteolipid and the like; glycoproteins such as ovomucoid, kallidin, bradykinin and the like; inhibitors against enzymes, such as antipain, pepstatin and the like; plasma proteins such as antitrypsin, ceruloplasmin, haptoglobin, macroglobulin, hemopexin, transferrin, glycoprotein, prothrombin, fibrinogen and the like; toxic proteins such as erabutoxin, butulinus toxin, cardiotoxin, bungarotoxin, ricin, abrin and the like; hormones such as angiotensin, glucagon, oxytocin, vasopressin, argininevasotocin, insulin, somalotropic hormones, lactogenic hormone, adrenocorticotropic hormone, somatotropic hormones, melanocyte stimulating hormones and the like; antibiotics such as gramicidins, collistin, tyrocidines, bacitracin, polymyxin and the like; enzymes; and the like.

Specific examples of the enzymes include oxidoreductases such as alcohol dehydrogenase (1.1.1.1), glcerol dehydrogenase (1.1.1.6), glycerol phosphate dehydrogenase (1.1.1.8), $\beta$-hydroxybutyrate dehydrogenase (1.1.1.30), malate dehydrogenase (1.1.1.37), isocitrate dehydrogenase (1.1.1.41), lactate dehydrogenase (1.1.1.27), galactose dehydrogenase (1.1.1.48), glucose-6-phosphate dehydrogenase (1.1.1.49), glucose oxidase (1.1.3.4), cholesterol oxidase (1.1.3.6), galactose oxidase (1.1.3.9), xanthine oxidase (1.2.3.2), glutamate dehydrogenase (1.4.1.2), L-amino-acid oxidase (1.4.3.2), D-amino-acid oxidase (1.4.3.3), pyridine nucleotide transhydrogenase (1.6.1.1), uricase (1.7.3.3), cytochrome (1.9.3.1), tyrosinase (1.10.3.1), catalase (1.11.1.6), peroxidase (1.11.1.7), lipoxygenase (1.13.1.13) and the like; transferases such as transaldolase (2.2.1.2), phosphorylase (2.4.1.1), dextransucrase (2.4.1.5), levansucrase (2.4.1.14), purine nucleoside phosphorylase (2.4.2.1), trans-N-glycosidase (2.4.2.6), glutamic-pyruvic transaminase (2.6.1.2), hexokinase (2.7.1.1), pyruvate kinase (2.7.1.40), carbamate kinase (2.7.2.2), phosphoglycerate kinase (2.7.2.3), creatine kinase (2.7.3.2), NAD pyrophosphorylase (2.7.7.1), RNA nucleotidyltransferase (2.7.7.6), polynucleotide phosphorylase (2.7.7.8), ribonucease (2.7.7.16) and the like; hydrolases such as lipase (3.1.1.3), acetylcholinesterase (3.1.1.7), cholesterol esterase (3.1.1.13), lipoprotein lipase (3.1.1.34), alkaline phosphatase (3.1.3.1), acid phosphatase (3.1.3.2), phosphodiesterase (3.1.4.1), deoxyribonuclease (3.1.4.5), $\alpha$-amylase (3.2.1.1), $\beta$-amylase (3.2.1.2), cellulase (3.2.1.4), dextranase (3.2.1.11), pectinase (3.2.1.15), lysozyme (3.2.1.17), neuraminidase (3.2.1.18), $\alpha$-galactosidase (3.2.1.22), $\beta$-galactosidase (3.2.1.23), invertase (3.2.1.26), hyaluronidase (3.2.1.35), leucine aminopeptidase (3.4.1.1), carboxypeptidase (3.4.2.3), prolidase (3.4.3.7), pepsin (3.4.4.1), renin (3.4.4.3), urokinase, trypsin (3.4.4.4), elastase (3.4.4.7), papain (3.4.4.10), ficin (3.4.4.12), renin, thrombin (3.4.4.13), subtilisin (3.4.4.16), subtilopeptidase A (3.4.4.16), chymotrypsin (3.4.4.5), kallikrein (3.4.21.8), asparaginase (3.5.1.1), glutaminase (3.5.1.2), urease (3.5.1.5), penicillin amidase (3.5.1.11), aminoacylase (3.5.1.14), penicillinase (3.5.2.6), adenine deaminase (3.5.4.2), ATPase (3.6.1.3), myosin ATPase (3.6.1.3), apyrase (3.6.1.5), ATP deaminase, AMP deaminase, glucosidase, subtilisin, cephalosporin acylase and the like; lyases such as aspartate 4-decarboxylase (4.1.1.12), aldolase (4.1.2.7), amino acid decarboxylase, fumarase (4.2.1.2), tryptophanase, 2-phosphoglycerate dehydrase (4.2.1.11), tryptophan synthase (4.2.1.20), aspartase (4.3.1.1), cysteine desulphhydrase (4.4.1.1) and the like; isomerases such as amino acid racemase, glucosephosphate isomerase (5.3.1.9), glucose isomerase and the like; ligases such as succinyl-CoA synthetase (6.2.1.4), citrate acid synthase and the like. Numbers given in the parentheses are in accordance with Enzyme Nomenclature (Recommendations of the International Union of Biochemistry on the Nomenclature and Classification of Enzyme).

By virtue of the foregoing various characteristics, the protein adsorbent of the present invention can be applied effectively to various uses as described hereinafter.

(1) Purification and Separation of Proteins:

The adsorbent of the present invention can adsorb effectively and selectively proteins contained in aqueous media due to very excellent selective adsorbing characteristics to proteins.

Adsorption of proteins from protein solutions or protein dispersions by using the adsorbent of the present invention is usually conducted at a pH of 7 but can be conducted at a pH within the broad range of from 1 to 11. The pH value suitable for the adsorption operation depends on the stability and isoelectric point of a protein to be adsorbed, and, hence, is determined depending on the kind of the protein to be adsorbed. In adsorption operation, it is recommended that the protein is dissolved in a buffer solution so that the pH can be kept constant. As examples of types of buffer solutions, there can be mentioned glycine-sodium chloride-hydrochloric acid type, acetic acid-sodium acetate type, potassium dihydrogenphosphate-disodium hydrogenphosphate type, sodium hydroxide-sodium chloride-glycine type, tris (hydroxymethyl) aminomethane type and the like. The adsorption operation may be carried out at temperatures ranging from 2° C. to 95° C., preferably from 5° C. to 60° C., especially preferably from 10° C. to 40° C. At too high a temperature, there is a possibility that the protein deteriorates. At too low a temperature, it is probable that the adsorption velocity of a protein decreases.

Generally, according to the present invention, adsorption of a protein may be effected by contacting the adsorbent of the present invention with a solution or a dispersion of the protein. Illustrative explanation of the method of adsorption is given hereinbefore.

Adsorption of proteins can be accomplished by adding the adsorbent of the present invention to protein solutions or protein dispersions (batch process). The adsorbent of the present invention may be employed for adsorption without drying after copolymerization. The amount of the adsorbent t be used, per liter of a solution or dispersion to be treated, is required to be in the range of from 0.02 g to 300 g, preferably from 0.1 g to 200 g, more preferably from 1 g to 100 g on a dry basis. Since the larger the amount of the adsorbent, the larger the amount of the protein adsorbed and the faster the adsorption velocity, the amount of the adsorbent to be used should be determined depending on the amount of the protein to be adsorbed and the desired time of adsorption. The adsorption time may be preferably in the range of from 1 minute to 500 hours, more preferably from 5 minutes to 200 hours. According to need, agitation or shaking is conducted to facilitate the adsorption and to shorten the time required for the adsorption. When such agitation or shaking is conducted, the adsorption time may be in the range of from 10 seconds to 100 hours, more preferably from 1 minute to 50 hours, especially preferably from 10 minutes to 20 hours.

Adsorption of proteins can also be accomplished by passing protein solutions or protein dispersions through a column or filter packed with the adsorbent of the present invention (continuous process). The quantitative relationship between the adsorbent and the solution or dispersion to be treated is almost the same as that in a batch process. In this continuous process, the space velocity of the solution or dispersion to be treated may be in the range of from $0.01 \ hr^{-1}$ to $1,000 \ hr^{-1}$, preferably from $0.02 \ hr^{-1}$ to $500 \ hr^{-1}$, more preferably from $0.04 \ hr^{-1}$ to $100 \ hr^{-1}$. Too large the space velocity results in pressure drop and/or reduction of adsorption rate.

Inorganic or organic salts may be added to a protein solution or dispersion in order to adjust the pH, increase the solubility of the protein and/or increase the amount of the protein to be adsorbed. Specific examples of such salts include sodium chloride, potassium chloride, potassium dihydrogenphosphate, sodium acetate, sodium citrate and the like. The amount of the salt to be added may be generally not more than 30% by weight to that of the protein solution or dispersion, preferably not more than 20% by weight. For the same purpose, water-soluble organic substances may be added to the protein solution or dispersion. Specific examples of such water-soluble organic substances include acetone, methanol, ethanol, dimethylformamide and the like. The amount of the water-soluble organic substance to be added may be not more than 50% by weight to that of the protein solution or dispersion, preferably not more than 30% by weight, more preferably not more than 20% by weight.

The adsorption time may be appropriately decided according to the state and concentration of a protein solution to be treated and to the adsorption system, the adsorption temperature and other conditions.

Before practical adsorption operation, setting of optimum conditions is required. This will be attained by determining quantitatively the adsorbing capacity of the adsorbent with the lapse of time. The protein-adsorbing capacity of the adsorbent was determined by the following procedures. Firstly, in case the adsorption was carried out by a batch process, the concentration of the protein in the treated solution or dispersion was determined. The amount of the protein adsorbed by the adsorbent was calculated from the difference between the concentration of the protein in the original solution or dispersion and that in the treated solution or dispersion. Secondly, in case the adsorption was carried out by a continuous process, after the adsorption, the protein solution or dispersion present among the grains of the adsorbent was washed out using the same solvent as that of the protein solution or dispersion. The volume of the solvent to be used for washing was 5 times the apparent volume of the adsorbent. The amount of the protein in the treated solution or dispersion including the washings was determined. The difference between the amount of the protein in the original solution or dispersion and that in the treated solution or dispersion is the amount of the protein adsorbed by the adsorbent. The protein-adsorbing capacity of the adsorbent is estimated in terms of mg of adsorbed protein per gram of dry adsorbent.

Recently, industrial applications of proteins have been investigated broadly in various fields, and accordingly, development of such adsorption method that is excellent in all the functional aspects as mentioned above, has been desired in the art. In this sense, the protein adsorbent and method of the present invention make great contributions in the art.

Adsorption chromatography, which is a typical instance of bench-scale separation and purification of natural organic compounds, utilizes the difference of the adsorbing force between an adsorbent and substances to be treated or a solvent molecule. In this separation and purification method, inorganic substances such as activated carbon, alumina, silica, calcium phosphate and magnesium silicate are now used as adsorbents. The adsorbent of the present invention is advantageous over these conventional adsorbents in various points. For example, the adsorbent of the present invention can be obtained in the state of a much better spherical shape, and the mechanical strength is very high and the adsorbent can be used repeatedly. Therefore, when the adsorbent of the present invention is used, it is possible to conduct adsorption chromatography on a large scale. Further, the adsorbent of the present invention is free from a defect often seen in inorganic adsorbents, namely the defect that substances to be separated are decomposed by the adsorbents, and therefore, the use of the adsorbent of the present invention makes it possible to handle unstable proteins very stably. Due to these advantages, the adsorbent of the present invention can be effectively used as a carrier for adsorption chromatography. Moreover, if the above-mentioned relationship between the pore diameter and the protein-adsorbing capacity is skillfully utilized, selective separation of proteins will also be possible.

Desorption of a protein adsorbed by the adsorbent of the present invention can be accomplished by weakening the adsorbing force between the adsorbent and the protein, for example, according to any of the following representative methods or a combination thereof.

(1) A method in which an eluting solution containing a salt is used, in case a protein solution or dispersion contains no salt.

(2) A method in which an eluting solution containing a salt of which the concentration is different from that of the salt in a protein solution or dispersion is used, in case the kind of the salt in the eluting solution is the same as that in the protein solution or dispersion.

(3) A method in which an eluting solution containing a different kind of a salt from that in a protein solution or dispersion is used.

(4) A method in which an eluting solution containing a water-soluble organic solvent is used, in case a protein solution or dispersion contains no water-soluble organic solvent.

(5) A method in which an eluting solution containing a water-soluble organic solvent of which the concentration is different from that of the solvent in a protein solution or dispersion is used, in case the kind of the solvent in the eluting solution is the same as that in the protein solution or dispersion.

(6) A method in which an eluting solution containing a different kind of a water-soluble organic solvent from that in a protein solution or dispersion is used.

(7) A method in which an eluting solution containing a detergent is used.

(8) A method in which desorption is carried out at a temperature different from that of adsorption.

(9) A method in which an eluting solution having a different pH value from that of a protein solution or dispersion is used.

Specific examples of the above-mentioned salts include sodium chloride, potassium chloride, potassium dihydrogen-phosphate, sodium acetate, sodium citrate and the like. Specific examples of the above-mentioned water-soluble organic solvents include acetone, methanol, ethanol, dimethylformamide and the like. Suitable conditions for the elution treatment may be chosen depending on the kind of the adsorbed protein to be eluted, and on the composition and the structure of the adsorbent.

(2) Removal of Proteins:

In some products, the quality is drastically degraded by incorporation of minute amounts of proteins. As an example of such products, there can be mentioned crude Japanese sake. Namely, crude Japanese sake is turbid with incorporation of proteins. When the adsorbent of the present invention is used, proteins contained in crude Japanese sake can be assuredly removed at high efficiency, and the quality of Japanese sake can be remarkably improved without any bad influence on properties of the product. Moreover, the protein-removing method using the adsorbent of the present invention is much advantageous over conventional methods such as a coagulation and precipitation method using persimmon tannin, a super centrifugal separation method and a separation method using an enzyme with respect to easiness of the adsorption operation and post treatment, and according to this method, proteins can be completely removed with economical advantages. This method is similarly adopted for clarification of brewages such as beer, wine and the like and of other products.

Further, the protein adsorbent of the present invention can be applied to removal of proteins from high protein content waste waters (e.g. waste waters discharged from a food processing process). In this case, the method using the protein adsorbent of the present invention is advantageous over conventional biological methods such as an activated sludge method and the like, because the treatment can be accomplished in a shorter time and the treatment space can be remarkably diminished.

(3) Use as Copolymer-Protein Composites:

Hereinbefore, utilization of the copolymer adsorbent itself of the present invention has been discussed. Hereinafter, usefulness of a composite comprising a porous copolymer and a protein will be discussed.

In the living body, there are present a variety of paired substances having specific interaction therebetween, for example, an enzyme and a substrate, an enzyme and an inhibitor, and an antigen and an antibody. One complex is formed from such paired substances. Some complexes are very stable, but some of other complexes are only temporarily present as intermediates and are readily decomposed. Enzyme-substrate complexes belong to the latter type. Among such substances, there are many proteins, and if they are adsorbed and fixed onto the adsorbent of the present invention, they can be applied to various uses.

An enzyme fixed onto a water-insoluble carrier is well-known as a immobilized enzyme. A method for preparing immobilized enzymes by physical adsorption is advantageous over the chemical bonding method in that the enzyme is hardly deteriorated by the fixing treatment and the carrier having the enzyme fixed thereto can be used continuously while supplying the enzyme afresh to the carrier. However, practical application of this method is not advanced because the adsorbing capacity of the carrier is low and the amount of the enzyme adsorbed on the carrier is limited.

In contrast, the protein adsorbent of the present invention has such a high protein-adsorbing capacity that at least several tens of mg of a protein can be adsorbed per gram of the dry copolymer. Further, the once adsorbed protein is hardly eluted by distilled water, deionized water and service water, and therefore, the composite comprising the adsorbent of the present invention and the enzyme adsorbed thereby can be applied as such to an enzymatic reaction.

Affinity chromatography is a separation method based on the principle that a physiologically active substance is fixed to a carrier and other physiologically active substance is separated by utilizing the interaction between the two physiologically active substances, and recently, this method has attracted great attention in the art. The adsorbent of the present invention will be effectively used as a carrier in practising this separation method. As typical instances of the substance to be adsorbed and fixed onto the adsorbent, there can be mentioned enzymes, antigens and antibodies. Incidentally, when these proteins are adsorbed on the adsorbent of the present invention, the use of a bifunctional reactant known as a protein cross-linking agent, such as glutaraldehyde or the like, does not cause any trouble. On the contrary, in this case, the bonding strength between the adsorbent and protein and the bonding strength between proteins themselves can be enhanced and the application range of the method can be broadened.

In case of a copolymer-protein composite, the amount of the protein is preferably at least 10 mg, more preferably at least 20 mg, per gram of the dry copolymer.

The present invention will now be described in detail by reference to the following Examples that by no means limit the scope of the invention.

EXAMPLE 1

A 3-liter three-neck flask equipped with a reflux condenser, a double-vane stirrer and a thermometer was charged with 55 g of acrylonitrile as distilled, 45% of divinylbenzene (having a purity of 56% and containing 44% of vinylethylbenzene as an impurity; hereafter referred to as "56% divinylbenzene"), 130 g of acetophenone, 120 g of decalin, 1 g of 2,2'-azobisisobutyronitrile and 1 g of 2,2'-azobis(2,4-dimethylvaleronitrile), and a homogeneous solution was prepared by stirring. Then, 1,270 g of distilled water containing, dissolved therein, 6.25 g of partially saponified polyvinyl acetate (having a viscosity of 23 cps as measured at 20° C. with respect to a 2% aqueous solution thereof and a degree of saponification of 88%) and 12.5 g of sodium chloride was added to the above solution, and the mixture was heated at 45° C. for 1 hour, at 50° C. for 2 hours, at 60° C. for 2 hours and at 70° C. for 4 hours while the mixture was agitated at 300 rpm. During the reaction, sampling was conducted at prescribed intervals, and a benzene extract of the sample was analyzed by gas chromatograph and the amount of the remaining monomers was measured to determine the yield of the copolymer. As a result, it was confirmed that under the above conditions, the yield of the copolymer was elevated to a level higher than 98%. Since the boiling point of acrylonitrile is low, it was necessary to enhance the efficiency of the reflux condenser by flowing cold water. The resulting copolymer was found to have a good spherical shape and the grain diameters were distributed in the range of from 60 to 120μ. After wet classification using a sieve of 200 mesh, unreacted monomers and organic liquids were removed with methanol. A part of the residual copolymer was taken out and dried at 60° C. under reduced pressure for 18 hours to form a sample for measurement by a porosimeter. The remainder of the copolymer product was washed with water repeatedly.

As a result of the measurement, it was found that the resulting copolymer was characterized by a bulk density of 0.21 g/ml, an average pore diameter of 1,200 Å and a total pore volume of 2.28 ml/g. It also was found that the volume of pores having a pore diameter in the range of 600 to 2,400 Å was 0.87 ml/g. This porous copolymer will be hereinafter referred to as "R-1".

EXAMPLE 2

A granular copolymer was prepared in the same manner as described in Example 1 except that the amounts added of acetophenone and decalin were changed to 200 g and 50 g, respectively. It was found that the grain diameters were distributed in the range of 80 to 140μ and the copolymer was characterized by a bulk density of 0.25 g/ml, an average pore diameter of 200 Å and a total pore volume of 1.83 ml/g. It also was found that the volume of pores having a pore diameter in the range of 100 to 400 Å was 0.86 ml/g.

This porous copolymer will be hereinafter referred to as "R-2".

EXAMPLE 3

A granular copolymer was prepared in the same manner as described in Example 1 except that 250 g of benzonitrile was added instead of the liquid mixture of acetophenone and decalin. It was found that the grain diameters were distributed in the range of 70 to 150μ and the copolymer was characterized by a bulk density of 0.28 g/ml, an average pore diameter of 80 Å and a total pore volume of 1.18 ml/g. It also was found that the volume of pores having a pore diameter in the range of 40 to 160 Å was 0.50 ml/g. This porous copolymer will be hereinafter referred to as "R-3".

COMPARATIVE EXAMPLE 1

The same flask as used in Example 1 was charged with 110 g of acrylonitrile, 90 g of 56% divinylbenzene, 2 g of 2,2'-azobisisobutyronitrile and 2 g of 2,2'-azobis(2,4-dimethylvaleronitrile), and 1,000 g of distilled water containing, dissolved therein, 5 g of the same partially saponified polyvinyl acetate as used in Example 1 and 15 g of sodium chloride were added to the charge of the flask. While the mixture was being agitated at 350 rpm, polymerization was conducted according to the same temperature schedule as adopted in Example 1, and the resulting reaction mixture was post-treated in the same manner as described in Example 1. The yield of the copolymer was found to be 97%. As a result of the measurement, it was found that the bulk density of the resulting copolymer was 0.62 g/ml, and the porosimeter measurement indicated that no porous structure was formed in the copolymer. This copolymer will be referred to as "C-1" hereinafter.

EXAMPLE 4

A copolymer was prepared in the same manner as described in Example 1 except that 100 g of acetophenone and 50 g of decalin were used as the liquids. It was found that the grain diameters were distributed in the range of 100 to 180μ and the copolymer was characterized by a bulk density of 0.31 g/ml, an average pore diameter of 1,100 Å and a total pore volume of 0.97 ml/g. It also was found that the volume of pores having a pore diameter in the range of 550 to 2,200 Å was 0.40 ml/g. This porous copolymer will be hereinafter referred to as "R-4".

EXAMPLE 5

The same flask as used in Example 1 was charged with 10 g of hydroxylapatite, 10 g of hydroxyethyl cellulose having a viscosity of 250 cps as measured at 20° C. with respect to a 2% aqueous solution thereof, 20 g of calcium chloride and 2,000 liters of distilled water, and the mixture was stirred at 70° C. to form a homogeneous solution. Then, the liquid temperature was lowered to 30° C., and while the aqueous solution was being agitated at 300 rpm, a homogeneous solution composed of 50 g of acrylonitrile, 10 g of ethylene glycol dimethacrylate, 40 g of styrene, 300 g of chlorobenzene, 0.25 of tert-butyl pervalerate and 0.75 g of benzoyl peroxide was added at a stroke to the above aqueous solution. The reaction was carried out according to the predetermined temperature schedule; namely, at 30° C. for 30 minutes, at 40° C. for 1 hour, at 50° C. for 2 hours, at 60° C. for 2 hours, at 70° C. for 2 hours and at 80° C. for 2 hours. The resulting copolymer was sufficiently washed with water and subjected to measurements of pore characteristics. It was found that the grain diameters were distributed in the range of 90 to 260μ and the copolymer was characterized by an average pore diameter of 500 Å and a total pore volume of 2.02 ml/g. It also was found that the volume of pores having a pore diameter in the range of 250 to 1,000 Å was 1.03 ml/g. This porous copolymer will be referred to as "R-5" hereinafter.

EXAMPLE 6

The same flask as used in Example 1 was charged with a mixed solution composed of 50 g of methacrylonitrile, 50 g of divinylbenzene having a purity of 80%, 200 g of ethylbenzene, 100 g of isooctanol and 1 g of lauroyl peroxide. A separately prepared suspending solution (1,650 g of an aqueous solution containing 8 g of methyl cellulose having a viscosity of 100 cps as measured at 20° C. with respect to a 2% aqueous solution thereof and 48 g of sodium chloride) was added to the charge of the flask, and while the mixture was being agitated at 200 rpm, it was heated at 60° C. for 1 hour, at 75° C. for 4 hours and at 90° C. for 3 hours. The resulting copolymer was washed with water and then subjected to measurements of the pore characteristics. It was found that the grain diameters were distributed in the range of 150 to 250μ and the copolymer was characterized by a bulk density of 0.20 g/ml, an average pore diameter of 3,000 Å and a total pore volume of 2.68 ml/g. It also was found that the volume of pores having a pore diameter in the range of 1,500 Å to 6,000 Å was 1.05 ml/g. This porous copolymer will be referred to as "R-6" hereinafter.

EXAMPLE 7

A 100-ml pressure-resistant glass vessel was charged with 20 g of acrylonitrile, 5 g of N,N'-ethylenediacrylamide, 0.2 g of 2,2'-azobis(2,4-demethylvaleronitrile), 30 g of dimethylformamide and 20 g of toluene, and the vessel was sealed and the mixture was agitated to form a homogeneous solution. The solution was heated at 40° C. for 2 hours, at 60° C., for 4 hours and at 80° C. for 2 hours. The sealed vessel was cooled and then broken, and the resulting copolymer was recovered, pulverized, classified according to the wet method using sieves of 80 to 200 mesh and washed with a sufficient amount of acetone to remove the liquid components. Then, the properties of the copolymer were determined by using a porosimeter. It was found that the copolymer was characterized by a bulk density of 0.26 g/ml, an average pore diameter of 800 Å and a total pore volume of 1.65 ml/g, and that the volume of pores having a pore diameter in the range of 400 to 1,600 Å was 0.73 ml/g. The porous copolymer will be referred to as "R-7" hereinafter.

EXAMPLE 8

In 10 ml of a solution containing 30 mg of a protein indicated in Table 1 was incorporated 0.5 g of the wet porous copolymer R-1, and the mixture was shaken at 30° C. for 3 hours. Precipitates were removed by centrifugal separation, and the concentration of the protein in the supernatant was measured according to the method of Lowry et al. (O. H. Lowry et al., J. Biol. Chem., 193, page 265, 1951). The difference between the thus determined protein concentration and the protein concentration measured with respect to the system free of the copolymer R-1 was designated as the amount of the adsorbed protein. With respect to urease, catalase, α-chymotrypsin and pepsin, also the residual enzymatic activity in the supernatant was measured.

Further, the enzymatic activities of the enzymes adsorbed on the copolymer were determined according to ordinary methods as set forth below.

Obtained results are shown in Table 1. The amount of the adsorbed protein is expressed in terms of mg per g of the dry copolymer.

Incidentally, the activity of urease was determined according to the method of D. D. Vanslyke et al. (J. Biol. Chem., 154, page 623, 1944) and the activity of catalase was determined according to the method of H. U. Bergmeyer (Biochem., Z., 327, page 255, 1955). Further, the activities of α-chymotrypsin and pepsin were determined according to the method of G. W. Schwert et al. (Biochem. Biophysica Acta., 16, page 570, 1955) and the method of L. M. Baker et al. (J. Biol. Chem., 211, page 701, 1954), respectively.

TABLE 1

| Protein | Molecular Weight | Isoelectric Point | Amount (mg) of Adsorbed Protein | Activity (%) of Adsorbed Enzyme | Residual Activity (%) of Enzyme in Supernatant |
|---|---|---|---|---|---|
| Jack bean urease | 470,000 | 5.0-5.1 | 160 | 11 | 33 |
| Catalase of | 240,000 | | 60 | 3 | 73 |

TABLE 1-continued

| Protein | Molecular Weight | Isoelectric Point | Amount (mg) of Adsorbed Protein | Activity (%) of Adsorbed Enzyme | Residual Activity (%) of Enzyme in Supernatant |
|---|---|---|---|---|---|
| bovine liver | | | | | |
| Human γ-globulin | 160,000 | 5.8–7.3 | 100 | — | — |
| Human hemoglobin | 68,000 | 6.8–7.0 | 110 | — | — |
| Ovalbumin | 45,000 | 4.7 | 90 | — | — |
| Pepsin | 35,000 | 1.0 | 120 | 10 | 50 |
| α-Chymotrypsin of bovine pancreas | 25,000 | 9.1 | 110 | 8 | 45 |

EXAMPLE 9

According to the same method as described in Example 8, trypsin (having a molecular weight of 20,000 and an isoelectric point of 10.0) was adsorbed on the porous copolymer R-1. The amount of the adsorbed protein was 130 mg per g of the dry copolymer, and the residual enzymatic activity in the supernatant was 45%. The resulting copolymer-protein composite was packed in a column and 0.05 M tris(hydroxymethyl)aminomethane buffer solution of benzoylarginine ethyl ester hydrochloride as a substrate (concentration=34 g/liter, pH=8.0) was flowed through the column at a space velocity at 2 hr$^{-1}$. The relative activity of the adsorbed enzyme was 70% when the contact had been conducted for 96 hours.

Incidentally, the activity of trypsin was determined according to the method of G. W. Schwert et al. (Biochem., Biophysica Acta., 16, page 570, 1955).

EXAMPLE 10 AND COMPARATIVE EXAMPLE 2

According to the same method as described in Example 8, the amounts of the protein adsorbed on the porous copolymers R-2 and R-3 were determined with respect to the proteins shown in Table 1 and trypsin. Obtained results are shown in Table 2.

For comparison, the amounts of these proteins adsorbed on the non-porous resin C-1 were determined, and obtained results are shown in Table 2.

TABLE 2

| Protein | Amount of Adsorbed Protein (mg/g of dry copolymer) | | |
|---|---|---|---|
| | R-2 | R-3 | C-1 |
| Urease | 20 | 10 | 0 |
| Catalase | 30 | 20 | 0 |
| γ-Globulin | 10 | 0 | 0 |
| Hemoglobin | 110 | 50 | —* |
| Ovalbumin | 50 | 30 | 10 |
| Pepsin | 80 | 60 | —* |
| α-Chymotrypsin | 130 | 80 | 10 |
| Trypsin | 140 | 80 | 5 |

Note
—* : not measured

EXAMPLE 11

According to the same method as described in Example 8, a protein shown in Table 3 was adsorbed on the copolymer R-1, and the copolymer-protein composite was packed in a column. Then, the composite was washed with water in a volume 3 times the capacity of the column and the protein was eluted with an eluting solution in a volume 5 times the capacity of the column. Obtained results are shown in Table 3.

TABLE 3

| Protein | Molecular Weight | Isoelectric Point | Amount of adsorbed Protein (mg/g of dry copolymer) | Eluting Solution | Protein Recovery Ratio (%) |
|---|---|---|---|---|---|
| Albumin of human serum | 65,000 | 4.7 | 170 | 20% (V/V) acetone | 91 |
| Cytochroma C of equine heart | 13,000 | 10 | 30 | 0.2M phosphate buffer | 70 |
| Bacitracin | 1,400 | 7 | 130 | 0.1N HCl | 85 |

EXAMPLE 12 AND COMPARATIVE EXAMPLE 3

The amounts of the protein adsorbed on the porous copolymers R-2 and R-3 were determined with respect to the proteins shown in Table 3 according to the same method as described in Example 8, to obtain results shown in Table 4. For comparison, the amounts of the proteins adsorbed on the non-porous resin C-1 was similarly determined. Obtained results are shown in Table 4.

TABLE 4

| Protein | Amount of Adsorbed Protein (mg/g of dry copolymer) | | |
|---|---|---|---|
| | R-2 | R-3 | C-1 |
| Serum albumin | 180 | 100 | —* |
| Cytochrome C | 30 | 10 | 0 |

TABLE 4-continued

| Protein | Amount of Adsorbed Protein (mg/g of dry copolymer) | | |
|---|---|---|---|
| | R-2 | R-3 | C-1 |
| Bacitracin | 150 | 120 | 20 |

Note
—* : not measured

EXAMPLE 13

Through a column having an inner diameter of 1.1 cm and packed with 10 ml of the porous copolymer R-1 was flowed at a space velocity of 10 hr$^{-1}$, 2 liters of crude Japanese sake prepared according to a customary method. Before and after the treatment, the liquid was subjected to super centrifugal separation (30 minutes under 50,000 G), and dry weights of precipitates obtained before and after the column treatment were measured and compared to obtain the following results.
Precipitate
Crude Japanese sake: 105 ppm
Treated Japanese sake: 5 ppm
Precipitate removal ratio: 95%

EXAMPLE 14

According to the same method as described in Example 8, the amounts of trypsin adsorbed on the porous copolymers R-4, R-5, R-6 and R-7 were determined to obtain results shown in Table 5.

TABLE 5

| Copolymer | Amount of Adsorbed Trypsin (mg/g of dry copolymer |
|---|---|
| R-4 | 80 |
| R-5 | 120 |
| R-6 | 100 |
| R-7 | 150 |

EXAMPLES 15 TO 18

Polymerization was conducted using the same flask as used in Example 1 in the same manner as described in Example 1 except the composition of the charge was different. The composition of the charge and the pore characteristics are shown in Table 6.

TABLE 6

| Example No. | Monomer | Liquid | Bulk Density | Average Pore Diameter (d) | Total Pore Volume | Pore Volume (0.5d to 2 d) |
|---|---|---|---|---|---|---|
| 15(R-15) | AN 10g DVB 90g | CH 20g IAA 180g | 0.22 g/ml | 1,400 Å | 1.88 ml/g | 0.77 ml/g |
| 16(R-16) | AN 46g DVB 54g | CH 66g IAA 154g | 0.19 g/ml | 500 Å | 1.52 ml/g | 0.61 ml/g |
| 17(R-17) | AN 64g DVB 36g | CH 40g IAA 160g | 0.19 g/ml | 2,800 Å | 1.99 ml/g | 0.98 ml/g |
| 18(R-18) | AN 82g DVB 18g | CH 100g IAA 100g | 0.17 g/ml | 2,400 Å | 1.44 ml/g | 0.60 ml/g |

Note
AN: acrylonitrile
DVB: 56% divinylbenzene
CH: cyclohexanone
IAA: isoamyl acetate
Pore Volume (0.5d to 2d): volume of pores having a pore diameter in the range of 0.5d to 2d
The resulting porous copolymers obtained in Examples 15 to 18 will be hereinafter referred as "R-15", "R-16", "R-17" and "R-18", resectively.

COMPARATIVE EXAMPLE 4

The same flask as used in Example 1 was charged with 20 g of acrylonitrile, 180 g of 56% divinylbenzene, 2 g of 2,2'-azobisisobutyronitrile and 2 g of 2,2'-azobis(2,4-dimethylvaleronitrile), and 1,000 g of pure water containing, dissolved therein, 5 g of the same partially saponified polyvinyl acetate as used in Example 1 and 15 g of sodium chloride was added to the charge. While the mixture was being agitated at 350 rpm, polymerization was carried out under the same temperature schedule as adopted in Example 1, and the post treatment was conducted in the same manner as described in Example 1. The yield of the copolymer was found to be 98%, and the bulk density of the resulting copolymer was 0.59 g/ml. Results of the measurements using a porosimeter indicated that pores were not present in the copolymer. This copolymer will be referred to as "C-4" hereinafter.

COMPARATIVE EXAMPLE 5

The same flask as used in Example 1 was charged with a homogeneous solution composed of 100 g of 56% of divinylbenzene, 80 g of tetralin, 120 g of cyclohexanol and 1 g of benzoyl peroxide, and 1,500 g of pure water containing, dissolved therein, 9 g of methyl cellulose (having a viscosity of 100 cps as measured at 20° C. with respect to a 2% aqueous solution thereof) was added to the above solution. The mixture was agitated at 60° C. for 1 hour, at 70° C. for 3 hours and at 80° C. for 4 hours to obtain a copolymer having a grain diameter of 60 to 200μ and a bulk density of 0.23 g/ml. Results of the measurements using a porosimeter indicated that the average pore diameter was 1,300 Å, the total pore volume was 1.63 ml/g and the volume of pores having a diameter of 650 Å to 2,600 Å was 0.53 ml/g. This porous copolymer will be referred to as "C-5" hereinafter.

EXAMPLE 19 AND COMPARATIVE EXAMPLE 6

According to the same method as described in Example 8, the amounts of the protein adsorbed on the porous copolymers R-15, R-16, C-4 and C-5 were determined to obtain results shown in Table 6.

Incidentally, serum albumin, α-chymotrypsin and lipase were used as the proteins to be tested.

TABLE 7

| | Amount of Protein Adsorbed (mg/g of dry copolymer) | | | |
|---|---|---|---|---|
| Protein | R-15 | R-16 | C-4 | C-5 |
| Serum albumin | 120 | 150 | 10 | 30 |
| α-Chymotrypsin | 90 | 90 | 5 | 20 |
| Lipase | 130 | 190 | 10 | 30 |

EXAMPLE 20

A mixture of 80 g of α-chloroacrylonitrile, 20 g of trimethylolpropane trimethacrylate, 300 g of toluene and 1 g of benzoyl peroxide was suspension-polymerized in an aqueous solution composed of 2,000 g of pure water, 20 g of carboxymethyl cellulose having a viscosity of 300 cps as measured at 20° C. with respect to a 2% aqueous solution thereof and 40 g of sodium chloride. The temperature schedule of polymerization and the post treatment were the same as described in Example 1. The pore characteristics of the resulting copolymer were as follows.

Average pore diameter: 5,000 Å
Total pore volume: 2.42 ml/g
Volume of pores having a pore diameter in the range of 2,500 to 10,000 Å: 1.36 ml/g

EXAMPLE 21

A mixture of 50 g of α-phenylacrylonitrile, 50 g of 80% divinylbenzene, 200 g of γ-butyrolactone and 2 g of 2,2'-azobisisobutyronitrile was suspension-polymerized in an aqueous suspension of 80 g of $BaSO_4$ and 10 g of methyl cellulose as used in Example 6 in 2,000 g of pure water. The temperature schedule of polymerization and the post treatment were the same as described in Example 1. The pore characteristics of the resulting copolymer were as follows.

Average pore diameter: 800 Å
Total pore volume: 2.03 ml/g
Volume of pores having a pore diameter in the range of 400 to 1,600 Å: 1.01 ml/g

EXAMPLE 22

10 g of the wet porous copolymer R-16 were added to 100 ml of a 0.1 M phosphate buffer solution (pH: 7.0) containing 50 mg of urease (760 units/mg) dissolved therein, which had been extracted from jack bean, and the resulting suspension was agitated at 25° C. for 4 hours. Then, the resulting composite comprising the copolymer and urease was packed in a column (inner diameter: 1.5 cm, height: 10 cm) equipped with a jacket and a glass filter, and 50 ml of a 25° C. 0.1 M phosphate buffer solution (pH: 7.0) was flowed down therethrough. Thereafter, a 0.1 M aqueous urea solution (pH: 7.0) was flowed down through the column at 37° C. at a flow rate of 200 ml/hr. According to determination of the obtained ammonia, the decomposition of urea was found to be 95%.

Incidentally, the enzymatic activity of urease was evaluated according to the following procedures. The enzymatic reaction of urea was conducted at a pH value of 7.0 at 37° C. and the obtained ammonia was determined according to Nessler's colorimetric analysis. The enzymatic activity of urease to obtain 1 micromole of ammonia per hour is evaluated as 1 unit.

EXAMPLE 23

1 g of the dry porous copolymer as shown in Table 8 was added to 10 ml of bovine serum containing 120 mg of proteins, and the resulting suspension was shaken at 35° C. for 2 hours. The proteins in the supernatant were estimated and the amount of the proteins adsorbed on the porous copolymer was determined. The results are shown in Table 8.

Incidentally, the estimation of the proteins was conducted according to an optical density measurement (278 mμ).

TABLE 8

| Copolymer | Amount of Adsorbed Proteins (mg/g of dry copolymer) |
|---|---|
| R-1 | 78 |
| R-16 | 63 |
| R-17 | 61 |
| R-18 | 58 |

COMPARATIVE EXAMPLE 7

According to substantially the same method as described in Example 1, a mixture of 90 g of 56% divinylbenzene, 10 g of styrene, 50 g of toluene, 100 g of sec-butanol and 1 g of benzoyl peroxide was suspension-polymerized. The pore characteristics of the resulting copolymer were as follows.

Average pore diameter: 200 Å
Total pore volume: 0.78 ml/g
This copolymer will be referred to as C-7.

COMPARATIVE EXAMPLE 8

1 g of the dry copolymer C-7 was packed in the same column as used in Example 22, and methanol was flowed down through the column and then 200 ml of water was flowed down through the column to prepare the wet copolymer. Using the thus prepared wet copolymer, substantially the same procedures as described in Example 22 were repeated. Adsorption of urease was not observed.

COMPARATIVE EXAMPLE 9

According to substantially the same method as described in Example 1, a mixture of 55 g of acrylonitrile, 45 g of 56% divinylbenzene, 30 g of decalin, 1 g of 2,2'-azobisisobutyronitrile and 1 g of 2,2'-azobis(2,4-dimethylvaleronitrile) was suspension-polymerized in an aqueous solution composed of 650 g of pure water, 3 g of partially saponified polyvinyl acetate as used in Example 1 and 6 g of sodium chloride. The pore characteristics of the resulting copolymer were as follows.

Average pore diameter: 600 Å
Total pore volume: 0.20 ml/g

The amount of the protein adsorbed on the obtained copolymer was determined, according to the same method as described in Example 8, to obtain results shown in Table 9.

TABLE 9

| Protein | Amount of Adsorbed Protein (mg/g of dry copolymer) |
|---|---|
| Catalase | 10 |
| Hemoglobin | 15 |
| Trypsin | 10 |
| Bacitracin | 25 |

EXAMPLE 24

The amounts of the protein adsorbed on the porous copolymer R-5, R-6, R-20 and R-21 were determined according to the following method. A glass column (inner diameter: 1.5 cm, height: 10 cm) with a jacket and a glass filter was packed with 2 g of the respective porous copolymer, and 50 ml of methanol was passed therethrough and then 200 ml of water was passed therethrough. Subsequently, 100 ml of water containing 100 mg of each of the proteins as shown in Table 10 were flowed down at 30° C. and at a space velocity of 4 $hr^{-1}$ and thereafter 10 ml of water were flowed down.

The flowed-down liquid was subjected to evaporation and the residual proteins were weighed to obtain results shown in Table 10.

TABLE 10

| Protein | Amount of Adsorbed Protein (mg/g of dry copolymer) | | | |
|---|---|---|---|---|
| | R-5 | R-6 | R-20 | R-21 |
| Γ-Globulin | 32 | 36 | 21 | 26 |
| Hemoglobin | 28 | 35 | 31 | 33 |
| Urease | 41 | 35 | 26 | 32 |
| Vasopressin | 29 | 31 | — | — |
| Fibrinogen | 38 | 19 | — | — |

EXAMPLE 25

A column (inner diameter: 1 cm, height: 10 cm) with a glass filter was packed with 5 g of the wet copolymer R-19. To 10 ml of bovine blood were added 1 mg of sodium salt of heparin and 90 ml of water. The resulting solution was passed through the column at 30° C. and at a space velocity of 15 hr$^{-1}$. Upon this operation, 98% of hemoglobin contained in the solution was adsorbed on the copolymer. The determination of hemoglobin was made by visible spectrum adsorption at 555 μm and 430 μm.

EXAMPLE 26

According to substantially the same method as described in Example 1, a mixture of 50 g of acrylonitrile, 30 g of styrene, 20 g of ethyleneglycol dimethacrylate, 100 g of toluene, 10 g of polystyrene having a molecular weight of 40,000 and 2 g of 2,2'-azobis(2,4-dimethylvaleronitrile) was suspension-polymerized in an aqueous solution composed of 1,000 g of pure water, 5 g of partially saponified polyvinyl acetate as used in Example 1 and 10 g of sodium chloride. The pore characteristics of the resulting copolymer were as follows.

Average pore diameter: 2,000 Å
Total pore volume: 0.82 ml/g
Volume of pores having a pore diameter in the range of 1,000 to 4,000 Å: 0.54 ml/g The amount of the protein adsorbed on the obtained porous copolymer was determined, according to the same method as described in Example 8, to obtain results shown in Table 11.

TABLE 11

| Protein | Amount of Adsorbed protein (mg/g of dry copolymer |
|---|---|
| Trypsin | 30 |
| Ovalbumin | 18 |
| Serum albumin | 42 |

COMPARATIVE EXAMPLE 10

According to substantially the same method as described in Example 1, suspension-polymerization was carried out using, as a monomer, 12 g of 56% divinylbenzene and 48 g of acrylonitrile, as an organic liquid, 260 g of toluene and 40 g of cyclohexanol, and, as an initiator, 0.4 g of 2,2'-azobisisobutyronitrile and 0.4 g of 2,2'-azobis(dimethylvaleronitrile). The obtained copolymer was so brittle that it readily collapsed in classification operation. Accordingly, the reaction mixture was put in a beaker and warm water of 50° C. was added to the mixture in an amount 10 multiple of that of the aqueous solution as used in the polymerization reaction. The so obtained mixture was gently stirred and then allowed to stand still and the resulting supernatant was removed. A series of these operations were repeated two times. Subsequently, similar operations were repeated two times using acetone in a volume 10 multiple of the apparent volume of the copolymer and further repeated two times using water. The pore characteristics of the obtained copolymer were as follows.

Average pore diameter: 1,500 Å
Total pore volume: 5.12 ml/g

A column having an inner diameter of 1 cm and a height of 10 cm was packed with 5 g of the wet copolymer and an aqueous solution of ovalbumin was passed through the column. The filter was clogged with the powder of the copolymer and the passage of the liquid was obstructed in the course of the adsorption operation.

The amount of the protein adsorbed on the copolymer was determined by the batch method according to the same method as described in Example 8. The amount of the protein adsorbed was 110 mg/g, but the bulk density was as low as 0.05. Thus, the amount of the adsorbed protein per unit volume was low and there was observed significant pulverizing of the copolymer even in the course of the batchwise adsorption operation.

What is claimed is:

1. A method for adsorbing a protein from an aqueous solution or dispersion of the protein which comprises contacting an aqueous solution or a dispersion of a protein with a porous copolymer obtained by copolymerizing a monomer mixture comprising 2 to 98% by weight of at least one cyano group-containing monomer represented by the following general formula (A):

(A)

wherein R stands for a hydrogen atom, an alkyl group having 1 to 10 carbon atoms, a halogen atom, a cyano group, a methoxy group, an acetoxyl group, or an unsubstituted or substituted phenyl group represented by the formula

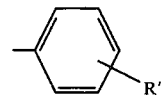

wherein R' stands for a hydrogen atom, an alkyl group having 1 to 10 carbon atoms, a halogen atom, a cyano group, a methoxy group or an acetoxyl group), and 2 to 98% by weight of at least one cross-linkable monomer having a plurality of CH$_2$=C< groups, said copolymer having an average pore diameter (d) of from 40 Å to 9,000 Å and a total pore volume of from 0.05 √X ml to 1.5 √X ml per gram of the copolymer in a dry state, in which X designates the weight proportion of said cross-linkable monomer expressed in terms of the percent by weight based on the total monomers, and being employed in an amount of 0.02 to 300 g per liter of said solution or said dispersion.

2. A method as set forth in claim 1 wherein the contacting of said solution or said dispersion with said porous copolymer is batchwise effected.

3. A method as set forth in claim 1 wherein the contacting of said solution or said dispersion with said porous copolymer is continuously effected.

4. A method as set forth in claim 1 wherein the contacting of said solution or said dispersion with said porous copolymer is effected at a temperature in the range of from 2° C. to 95° C.

5. A method as set forth in claim 2 wherein the contacting time is in the range of from 10 seconds to 500 hours.

6. A method as set forth in claim 3 wherein said solution or said dispersion is supplied at a space velocity in the range of from 0.01 hr$^{-1}$ to 1,000 hr$^{-1}$.

7. A method as set forth in claim 1 wherein said solution or said dispersion has a pH of from 1 to 11.

8. A composite comprising a porous copolymer and a protein in an amount sufficient to exert activity of said protein adsorbed thereon, said porous copolymer being a product obtained by copolymerizing a monomer mixture comprising 2 to 98% by weight of at least one cyano group-containing monomer represented by the following general formula (A):

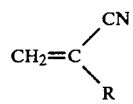

(A)

wherein R stands for a hydrogen atom, an alkyl group having 1 to 10 carbon atoms, a halogen atom, a cyano group, a methoxy group, an acetoxyl group, or an unsubstituted or substituted phenyl group represented by the formula

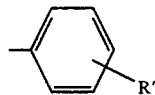

(wherein R' stands for a hydrogen atom, an alkyl group having 1 to 10 carbon atoms, a halogen atom, a cyano group, a methoxy group or an acetoxyl group), and 2 to 98% by weight of at least one cross-linkable monomer having a plurality of $CH_2=C<$ groups, said copolymer having an average pore diameter (d) of from 40 Å to 9,000 Å and a total pore volume of from 0.05 $\sqrt{X}$ ml to 1.5 $\sqrt{X}$ ml per gram of the copolymer in a dry state, in which X designates the weight proportion of said cross-linkable monomer expressed in terms of the percent by weight based on the total monomers.

9. A composite as set forth in claim 8 wherein the amount of the protein is at least 10 mg per gram of the copolymer in a dry state.

10. A composite as set forth in claim 9 wherein the amount of the protein is at least 20 mg per gram of the copolymer in a dry state.

11. A composite as set forth in claim 8, wherein the protein is an enzyme.

12. A method as set forth in claim 1 wherein the content of the cyano group-containing monomer is 4 to 95% by weight.

13. A method as set forth in claim 1 wherein the content of the cyano group-containing monomer is 6 to 90% by weight.

14. A method as set forth in claim 1 wherein the cyano group-containing monomer is a member selected from the group consisting of acrylonitrile, methacrylonitrile and mixtures thereof.

15. A method as set forth in claim 1 wherein the cross-linkable monomer is a monomer having 2 to 4 vinyl groups.

16. A method as set forth in claim 1 wherein the cross-linkable monomer is divinylbenzene.

17. A method as set forth in claim 1 wherein the cross-linkable monomer is of the formula

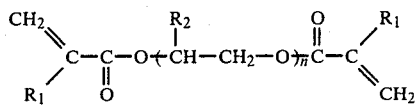

wherein $R_1$ and $R_2$ each independently is hydrogen or methyl, and n is an integer from 1 to 30.

18. A method as set forth in claim 1 wherein the weight proportion of the cross-linkable monomer is 8 to 80% by weight.

19. A method as set forth in claim 1 wherein the average pore diameter (d) of said porous copolymer is in the range of from 50 Å to 5,000 Å.

20. A method as set forth in claim 1 wherein the volume of pores of said porous copolymer having a diameter of 0.5 d to 2 d is not more than 60% of the total pore volume.

21. A method as set forth in claim 1 wherein the total pore volume of said porous copolymer is in the range of from 0.2 $\sqrt{X}$ ml to 1.3 $\sqrt{X}$ ml per gram of the copolymer in a dry state.

22. A method as set forth in claim 1 wherein the protein has a molecular weight of from 1,000 to 1,000,000.

23. A method as set forth in claim 1 wherein the protein is albumin of human serum.

24. A method as set forth in claim 1 wherein the protein is α-chymotrypsin.

25. A method as set forth in claim 1 wherein the protein is lipase.

26. A method as set forth in claim 1 wherein the protein is an enzyme.

27. A method as set forth in claim 1 wherein the protein is trypsin.

28. A method as set forth in claim 1 wherein the protein is chymotrypsin.

29. A method as set forth in claim 1 wherein the protein is an antigen.

30. A method as set forth in claim 1 wherein the protein is an antibody.

31. A method as set forth in claim 1 wherein said porous copolymer has a spherical shape.

32. A method as set forth in claim 31 wherein said porous copolymer is a product obtained by suspension polymerization which is carried out in an aqueous solution in the presence of a radical initiator.

33. A composite produced by the method of claim 1 which comprises the porous copolymer and the protein in an amount sufficient to exert activity of said protein adsorbed thereon.

34. A composite as set forth in claim 33 wherein the amount of said protein is at least 10 mg per gram of the copolymer in a dry state.

35. A composite as set forth in claim 34 wherein the amount of said protein is at least 20 mg per gram of the copolymer in a dry state.

36. A composite as set forth in claim 33 wherein the protein is an enzyme.

* * * * *